(12) United States Patent
Dreyfuss et al.

(10) Patent No.: US 9,463,011 B2
(45) Date of Patent: Oct. 11, 2016

(54) SOFT ANCHORS WITH SOFT EYELETS

(71) Applicant: Arthrex, Inc., Naples, FL (US)

(72) Inventors: Peter J. Dreyfuss, Naples, FL (US);
Thomas Dooney, Jr., Naples, FL (US);
E. Lyle Cain, Jr., Birmingham, AL (US); Jeffrey R. Dugas, Vestavia Hills, AL (US); Kyle Anderson, Birmingham, AL (US); Peter J. Millett, Vail, CO (US)

(73) Assignee: Arthrex, Inc., Naples, FL (US)

( * ) Notice: Subject to any disclaimer, the term of this patent is extended or adjusted under 35 U.S.C. 154(b) by 283 days.

(21) Appl. No.: 13/961,716

(22) Filed: Aug. 7, 2013

(65) Prior Publication Data

US 2014/0052179 A1    Feb. 20, 2014

Related U.S. Application Data

(60) Provisional application No. 61/684,418, filed on Aug. 17, 2012.

(51) Int. Cl.
*A61B 17/04* (2006.01)
*A61F 2/08* (2006.01)
*A61B 17/00* (2006.01)

(52) U.S. Cl.
CPC ....... *A61B 17/0401* (2013.01); *A61B 17/0485* (2013.01); *A61F 2/08* (2013.01); *A61F 2/0811* (2013.01); *A61B 2017/00526* (2013.01); *A61B 2017/0406* (2013.01);
(Continued)

(58) Field of Classification Search
CPC .................. A61B 17/0401; A61B 2017/0406; A61B 2017/0477; A61B 2017/0403–2017/0462; A61B 17/0485; A61B 2017/06166; A61B 2017/06185; A61B 17/12009; A61B 17/823; A61F 2/0811; A61F 2002/0852; A61F 2002/0817–2002/0888
USPC ...................................... 606/232; 623/13.14
See application file for complete search history.

(56) References Cited

U.S. PATENT DOCUMENTS 5,989,252 A    11/1999  Fumex
6,296,659 B1   10/2001  Foerster
(Continued)

FOREIGN PATENT DOCUMENTS

EP    2 277 457 A1    1/2011
WO    WO 2007/005394 A1    1/2007
WO    WO 2009/029914 A1    3/2009

OTHER PUBLICATIONS

R. Glousman et al., "JuggerKnot Soft Anchor," Labral Repair, Surgical Protocol, BIOMET Sports Medicine, www.biometsportsmedicine.com, 2010,2011.

*Primary Examiner* — Katherine M Shi
*Assistant Examiner* — Lindsey Bachman
(74) *Attorney, Agent, or Firm* — Blank Rome LLP

(57) ABSTRACT

Soft anchor constructs and methods for soft tissue to bone repairs. The soft anchors may be knotted or knotless constructs. The soft anchors include a body formed of various soft materials (including, but not limited to, suture) and provided in various shapes and configurations that confer the anchors the ability to be easily inserted within bone tunnels or sockets and be bunched up within the bone tunnels or sockets. At least one closed loop or soft eyelet is attached to the soft anchor to allow additional sliding strands and/or shuttle/pull devices (suture passing devices) to pass through the eyelet and aid in the knotted or knotless fixation of tissue to bone.

16 Claims, 15 Drawing Sheets

(52) U.S. Cl.
CPC ............... *A61B 2017/0417* (2013.01); *A61B 2017/0477* (2013.01); *A61F 2002/087* (2013.01); *A61F 2002/0852* (2013.01); *A61F 2002/0888* (2013.01)

(56) References Cited

U.S. PATENT DOCUMENTS

| | | |
|---|---|---|
| 6,511,498 B1 | 1/2003 | Fumex |
| 6,716,234 B2 | 4/2004 | Grafton et al. |
| 7,329,272 B2 | 2/2008 | Burkhart et al. |
| 7,803,173 B2 | 9/2010 | Burkhart et al. |
| 7,892,256 B2 | 2/2011 | Grafton et al. |
| 8,118,836 B2 | 2/2012 | Denham et al. |
| 2007/0135843 A1 | 6/2007 | Burkhart |
| 2007/0185532 A1 | 8/2007 | Stone et al. |
| 2008/0027446 A1 | 1/2008 | Stone et al. |
| 2009/0306711 A1 | 12/2009 | Stone et al. |
| 2009/0318961 A1 | 12/2009 | Stone et al. |
| 2011/0098727 A1* | 4/2011 | Kaiser ............... A61B 17/0401 606/144 |
| 2011/0264141 A1 | 10/2011 | Denham et al. |
| 2012/0150203 A1 | 6/2012 | Brady et al. |
| 2013/0110165 A1 | 5/2013 | Burkhart et al. |
| 2013/0144337 A1* | 6/2013 | Stone ............... A61B 17/0401 606/232 |
| 2013/0296934 A1* | 11/2013 | Sengun ............. A61B 17/0401 606/232 |

* cited by examiner

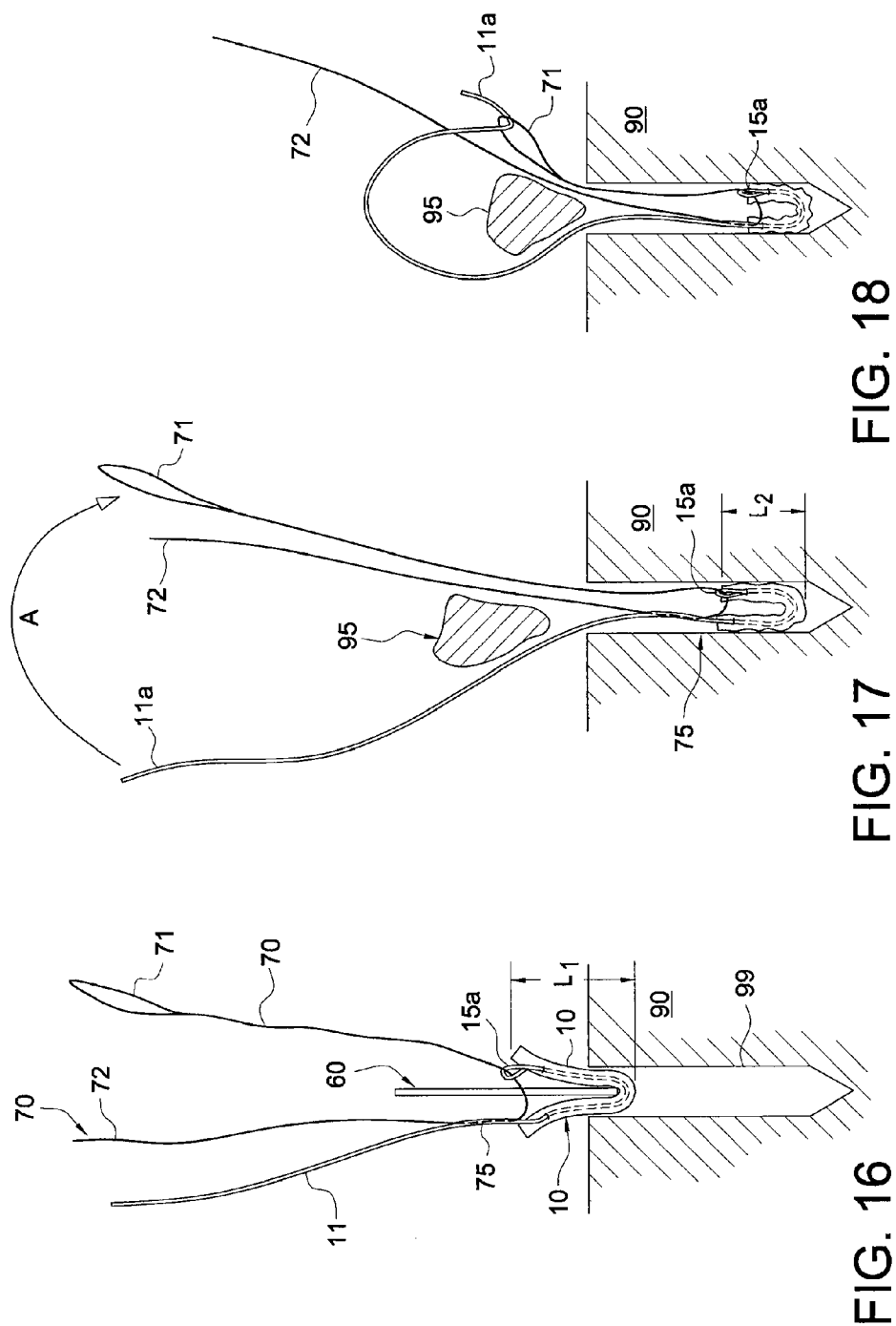

SOFT ANCHORS WITH SOFT EYELETS

CROSS-REFERENCE TO RELATED APPLICATIONS

This application claims the benefit of U.S. Provisional Application No. 61/684,418 filed Aug. 17, 2012, the disclosure of which is incorporated by reference in its entirety herein.

FIELD OF THE INVENTION

The present invention relates to surgical devices and, in particular, to soft suture-based anchors.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

It would be desirable to provide a suture construct that may be knotted or knotless and that is formed essentially of a soft material such as suture (or suture-based materials or other soft materials and/or compositions) with the ability to be inserted into a bone socket but also having tying, sliding sutures that are allowed to run/slide freely. Also needed is a soft, suture-based anchor that is knotless and is provided with an independent, soft suture eyelet and a self-cinching mechanism connected to both the independent, soft suture eyelet and to the suture-based anchor.

SUMMARY OF THE INVENTION

The present invention provides soft anchors which are designed to be inserted into the bone and which have flexible strand(s) within the body of the anchors. The soft anchors may be knotted or knotless constructs. The soft anchors include a body formed of various soft materials (including, but not limited to, suture) and provided in various shapes and configurations that confer the anchors the ability to be easily inserted within bone tunnels or sockets and be bunched up within the bone tunnels or sockets. At least one closed loop or soft eyelet is attached to the soft anchor to allow additional sliding strands and/or a shuttle/pull device (suture passing device) to pass through the eyelet and aid in the knotted or knotless fixation of tissue to bone.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 16-20 illustrate subsequent steps of a method of attaching soft tissue to bone with the soft anchor of FIG. 15 and according to an exemplary embodiment of the present invention.

DETAILED DESCRIPTION OF THE EMBODIMENTS

Figure 1:
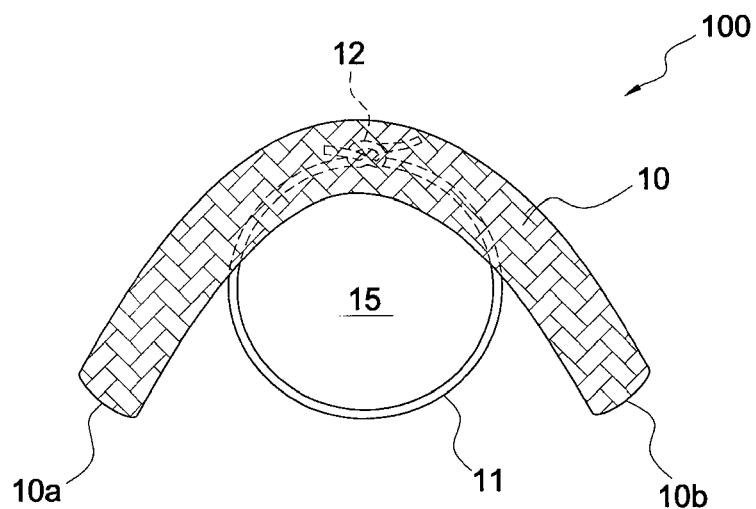
FIG. 1 illustrates a soft anchor according to an exemplary embodiment of the present invention.

The present invention provides surgical systems and methods for knotted or knotless soft tissue (ligament, tendon, graft, etc.) repair and fixation, such as fixation of soft tissue to bone. The surgical systems of the present invention include fixation devices in the form of soft anchors that are formed of various soft materials and are provided in various shapes and configurations that confer the anchors the ability to be easily inserted within bone tunnels or sockets and be bunched up within the bone tunnels or sockets. The soft anchors are formed essentially of soft materials such as yarns, fibers, filaments, strings, fibrils, strands, sutures, etc. or combinations of such soft materials. The soft materials may be synthetic or natural materials, or combinations of synthetic and natural materials, and may be degradable or non-degradable or combinations thereof At least one closed loop or soft eyelet is attached to the body of the anchor to allow additional sliding flexible strands and/or shuttle/pull devices (suture passing devices) to pass through the eyelet and aid in the fixation of tissue to bone.

The soft anchors may be knotted or knotless. As detailed below, an exemplary knotted soft anchor includes (i) an anchor body, (ii) a securing strand that extends through at least a portion of the body and forms a closed loop and/or at least one soft eyelet, and (iii) a tissue attachment strand (knot tying suture) that attaches to the closed loop and/or the at least one soft eyelet, and secures the tissue to be fixated by having knots tied in.

As detailed below, an exemplary knotless soft anchor includes (i) an anchor body, and (ii) a securing strand that extends through at least a portion of the body, the securing strand having, at one end, a closed loop and/or at least one soft eyelet and, at a portion of the other end, a self-cinching assembly (a spliced loop). The self-cinching assembly (splice loop) may be formed with a shuttle/pull device (for example, a suture passing instrument such as a wire suture passer) attached to the construct.

The anchors have a body in the form of any sleeve/sheath structure which may be provided with open or closed ends, or with at least one open end or with at least one opening on the side of the body for the securing strand to exit the body on a sidewall of the body (i.e., not at the end of the body). The anchors may also have a tubular shape, partially tubular shape, or may be in the form of a hollow shape construct. The anchors have a body which may be a woven, braided or knitted structure, and/or may be formed of yarns, fibers, filaments, sutures or similar materials, or combinations of such materials. The anchor body is typically without a core. In exemplary-only and non-limiting embodiments, the soft anchors include a body that is formed essentially of suture. The suture-based anchor body may be any woven, braided structure including, but not limited to, suture formed of polyester, polyethylene or any other suture material. If the anchor is knotless, the securing strand is preferably formed of a coreless suture to accommodate the splicing.

The securing strand that attaches to the anchor body may be any type suture, including coreless sutures that form a closed loop, or two eyelets each at one end of the strand (i.e., in a dumbbell shape), or an eyelet at one end and a shuttle/pull device (a suture passing instrument such as a wire suture passer) at the other end to form a spliced loop. The securing strand can extend through the open ends of the sleeve/sheath or through an opening in the sleeve body. Once the anchor body is inserted into a bone tunnel or socket it bunches up securing the anchor in the tunnel. The securing strand does not necessarily have to be engaged to accomplish the bunching of the anchor.

The tissue attachment strand may be any flexible strand (for example, suture) and may be pre-assembled to hold the anchor onto an inserter. The tissue attachment strand is the strand that attaches to the tissue and gets knots tied in it, and that also holds the construct to an inserter instrument to keep the construct at the bottom of the bone hole/socket. For the knotless anchors, and as described below, the securing strand becomes the tissue attachment strand (this strand does not require a knot to secure the tissue, the splice accomplishes the locking). For the knotless anchors, an attachment suture is used to hold the anchor onto the inserter during the insertion process and then removed once the anchor is in the bone hole/socket.

Referring now to the drawings, where like elements are designated by like reference numerals, FIGS. 1-20 illustrate exemplary soft anchors 100, 200, 100a, 200a of the present invention that are formed essentially of a flexible, soft material such as suture (for example, a polyester sheath) or any other similar soft materials. Soft anchor 100 and 100a are exemplary knotted embodiments. Soft anchors 200 and 200a are exemplary knotless embodiments.

Figure 2:
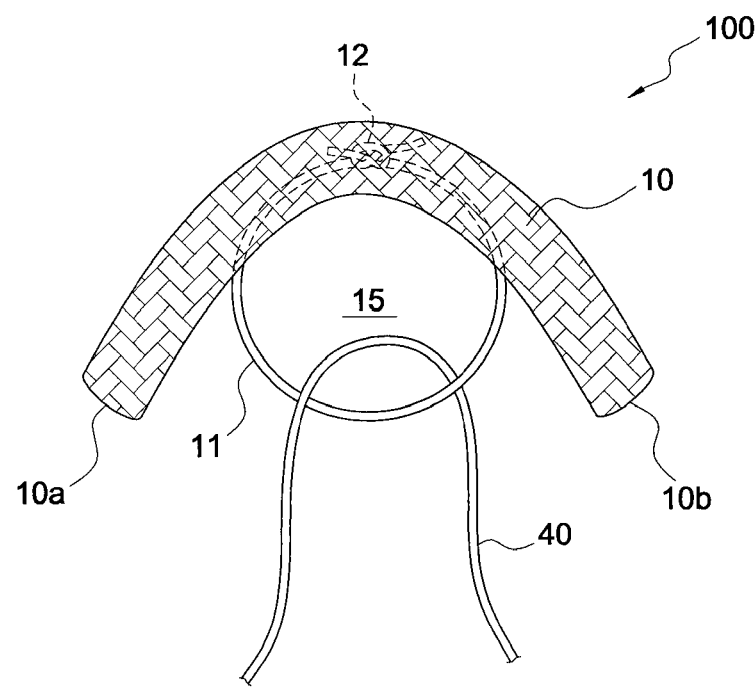
FIG. 2 illustrates the soft anchor of FIG. 1 with at least one sliding suture passing through the eyelet of the anchor.
Figure 3:
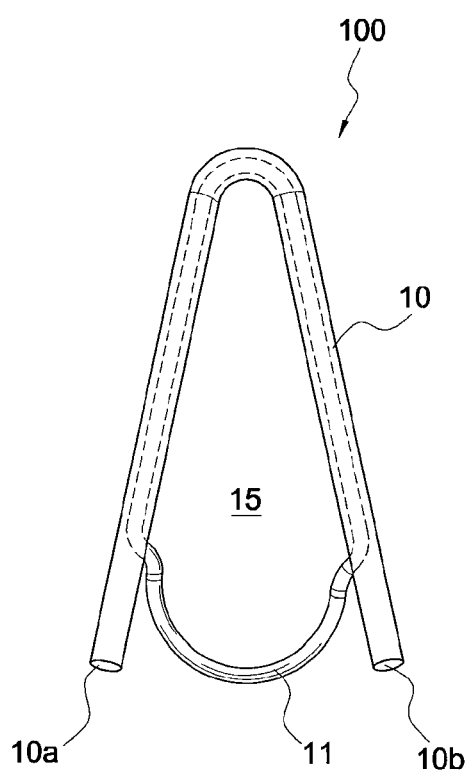
FIGS. 3 and 4 illustrate additional views of the soft anchor of FIG. 1 (showing the positioning of the eyelet relative to the body of the anchor).
Figure 4:
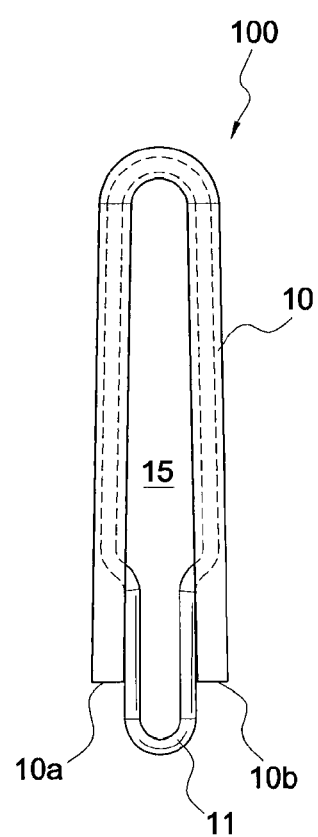

FIGS. 1-4 illustrate soft anchor 100 formed essentially of anchor body 10 in the form of a flexible material 10 (for example, a braided suture such as a polyester sheath/sleeve/ tube 10) and a securing strand 11 which forms a soft independent closed loop 15 attached to the anchor body 10. Closed loop 15 may be formed by tying a knot or splicing. For example, FIGS. 3 and 4 show closed loop 15 formed by splicing while FIGS. 1 and 2 show the closed loop formed by providing knot 12 at the top in the middle of the U-shaped structure. The anchor body 10 may be in the form of any sleeve/sheath structure or tubular structure which may be provided with open or closed ends 10a, 10b (FIG. 1), or with at least one open end or with at least one closed end. The anchor body 10 may be a woven, braided or knitted structure, and/or may be formed of yarns, fibers, filaments, sutures or similar materials, or combinations of these materials, including, but not limited to, suture formed of polyester.

Securing strand 11 is a flexible strand that is passed through at least a portion of the length of the flexible material 10. The securing strand 11 attaches to the anchor body 10 and may be any type of suture, including coreless sutures that form closed loop 15. The securing strand 11 can extend through the open ends 10a, 10b of the sleeve/sheath 10 or through an opening in the sleeve body. The securing strand 11 may assist in bunching up the anchor body 10 (sleeve/sheath) once the anchor body 10 is inserted into a bone tunnel or socket. The securing strand 11 may be also attached to the anchor body 10 in a suture-through-suture technique (with a needle, for example). Strand 11 may be an exemplary FiberWire® or TigerWire® suture 11, and may circle back to exit through the sheath 10, creating a closed independent loop/eyelet 15. The strand forming the closed loop/eyelet 15 exits on one side of the anchor body and enters on the other side of the anchor body, so that there is a gap in the anchor where the closed loop is exposed. Loop/eyelet 15 is a soft loop/eyelet. In an exemplary-only embodiment, the securing strand 11 (the FiberWire® or TigerWire® suture 11) may be passed through the anchor body 10 at different locations and as desired, for example, at predetermined insertion points on the length of the anchor body. The end of the FiberWire® or TigerWire® suture 11 is brought back to reenter the anchor body 10 to form the closed loop 15.

FIG. 2 illustrates soft anchor 100 with at least another flexible strand 40 (a tissue attachment strand 40) passing through the closed loop 15. The tissue attachment strand 40 may be any flexible strand (for example, suture) and may be pre-assembled with the anchor on an inserter (similar to inserter 60 shown in FIG. 13). The tissue attachment strand 40 is the strand that attaches to the tissue to get fixated/ reapproximated and gets knots tied in it (and also holds the construct to the inserter to keep the construct at the bottom of the bone hole/socket).

When the soft anchor 100 is inserted into a bone socket/ tunnel employing an inserter instrument (for example, a pusher provided with a forked tip), the body of the anchor 100 bunches up within the bone socket/tunnel. However, the tissue attachment suture 40 remains free to slide untangled, to allow completion of the soft tissue repair, for example, to be passed through or around the soft tissue to be attached to the bone.

FIGS. 3 and 4 illustrate additional views of the soft anchor 100 of the present invention showing in more detail the securing strand 11 forming spliced closed loop 15 contained within the body of the exemplary sheath 10 (tubular construct 10).

A method of tissue repair with the exemplary construct 100 (soft knotted anchor 100) of the present invention comprises inter alia the steps of: (i) drilling/punching a hole in bone; (ii) inserting soft anchor 100 into the hole in the bone to compress the soft anchor into the hole; and (iii) tying free suture 40 around or through tissue and completing the repair tying knots.

Figure 5:
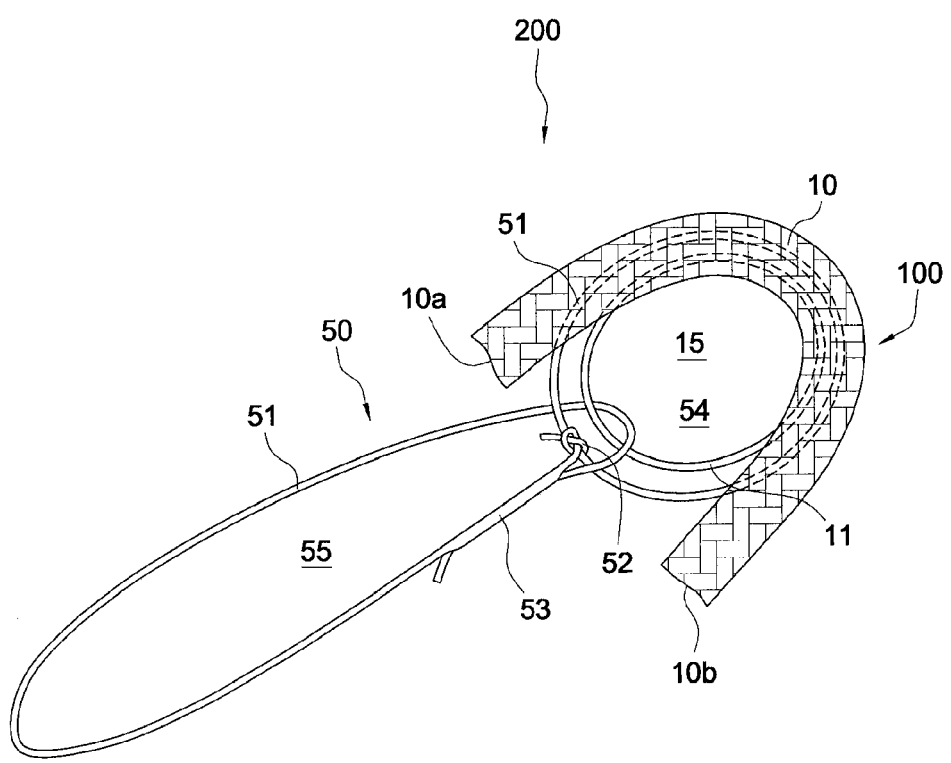
FIG. 5 illustrates a soft anchor according to another exemplary embodiment of the present invention (with a self-cinching loop passed around tissue and attached to the body of the anchor).

FIG. 5 illustrates another embodiment of the present invention. Soft anchor 200 is similar to the soft anchor 100 in that it also contains an anchor body 10 formed essentially of a soft material (for example, coreless suture such as a UHMWPE braided sheath/sleeve) and a securing strand 11 forming soft independent loop 15 attached to anchor body 10. However, the soft anchor 200 is a knotless—and not knotted—construct that contains a self-cinching construct 50 attached to the loop 15 (and to the braided sheath 10), as shown in FIG. 5. The self-cinching construct 50 may be formed prior or after the lodging of the soft anchor into bone, and eliminates the formation of any knots and the need for a tissue attachment strand (such as strand 40 of FIG. 2).

Self-cinching construct 50 may be formed by passing a length of flexible material 51 (for example, a cinching suture 51) through the length of the anchor body 10 (braided sheath/sleeve 10) two times with a needle, as shown in FIG. 5. The ends of strand 51 are then tied together to form a knot 52, closed loop 54 and closed loop 15 (both loops having a similar perimeter). The perimeter of loop 54 is fixed.

One end of the strand 51 is then passed through the loops 15, 54 and around (or through) tissue to be fixated, and then spliced through the remaining end, to form splice 53 and adjustable cinching loop 55 (shown in FIG. 5). The perimeter of cinching loop 55 is adjustable, to allow the construct to be self-cinching and to adjust the tension on the tissue to be fixated.

The assembly created by the cinching loop 55 uses the suture loop 15 (eyelet 15) as a turning point for application of force and to direct the cinching suture 51 into the construct in the correct manner.

Figure 6:
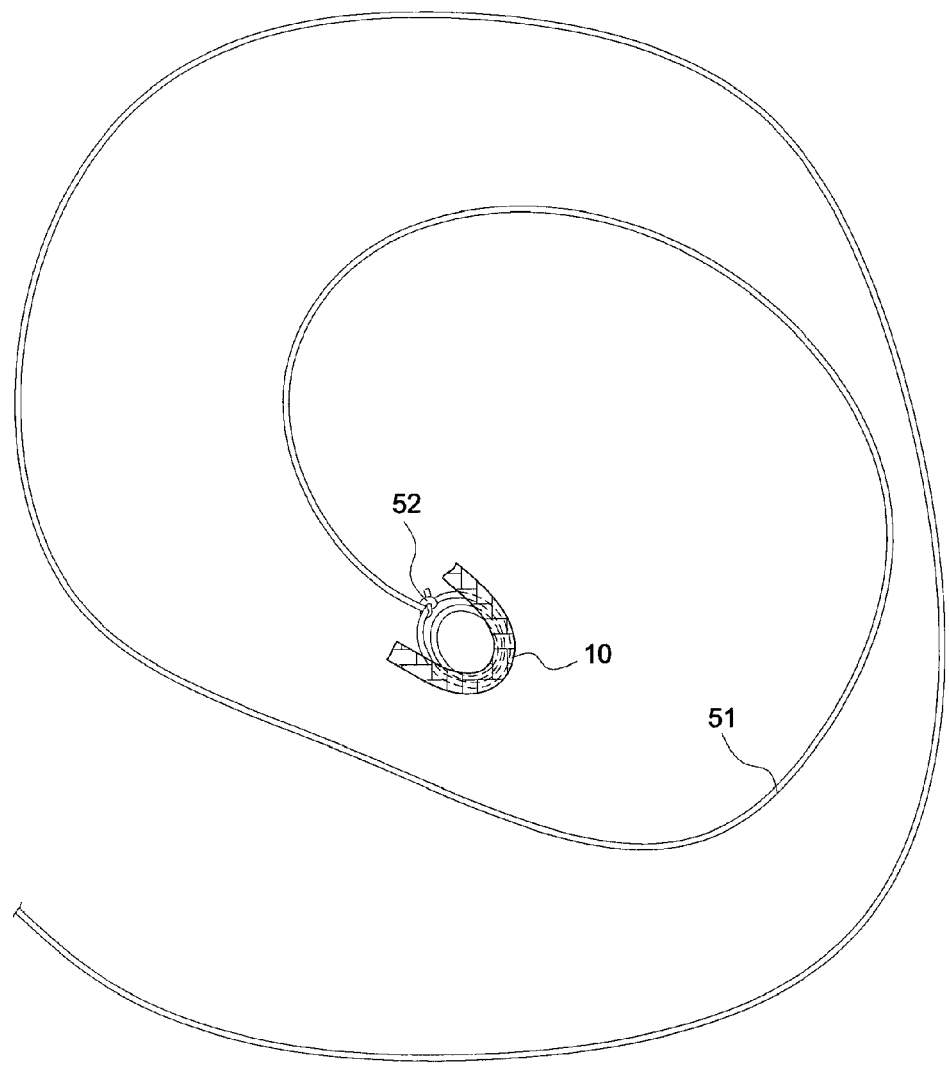
FIGS. 6-11 illustrate subsequent steps of a method of forming the soft anchor of FIG. 5 (with a self-cinching construct) and of employing the soft anchor for attachment of soft tissue to bone.
Figure 7:
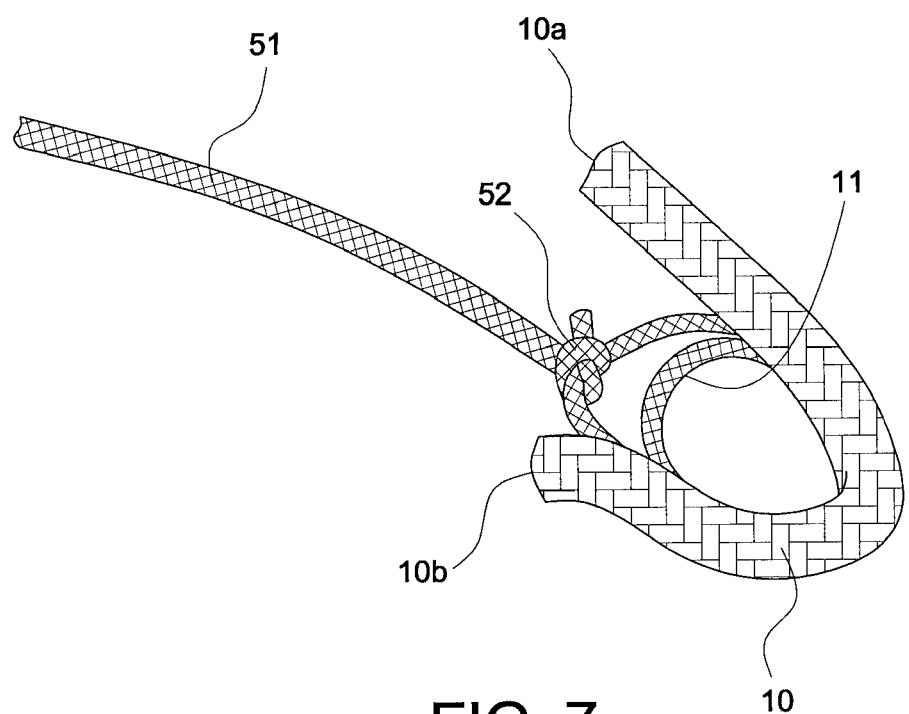
Figure 8:
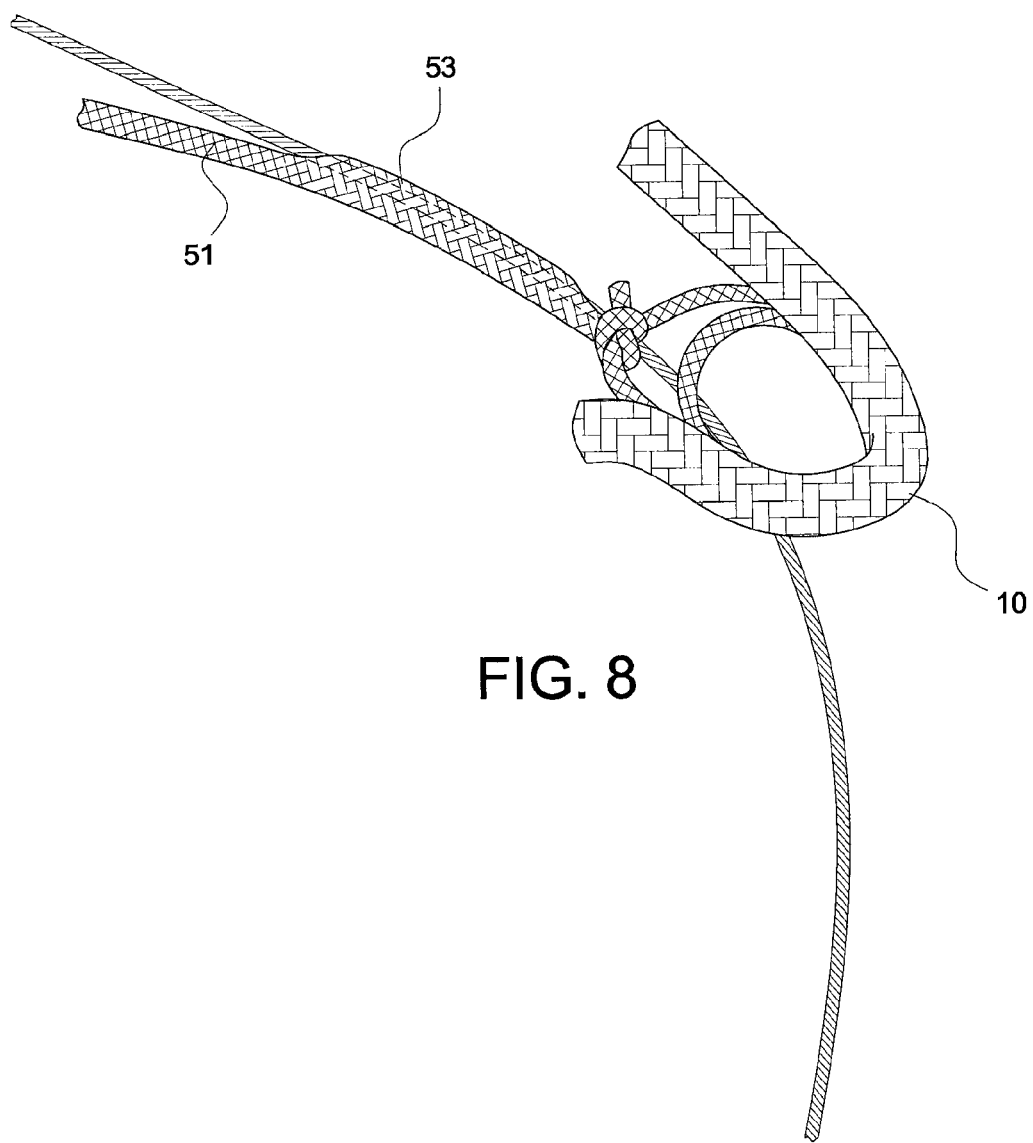
Figure 9:
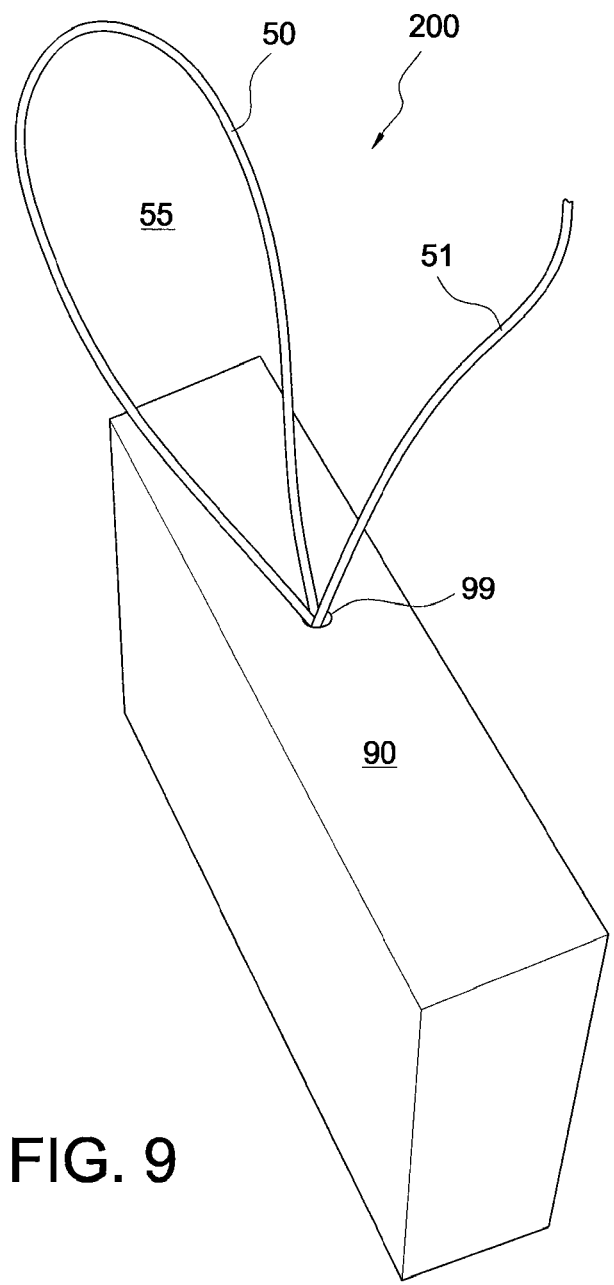
Figure 10:
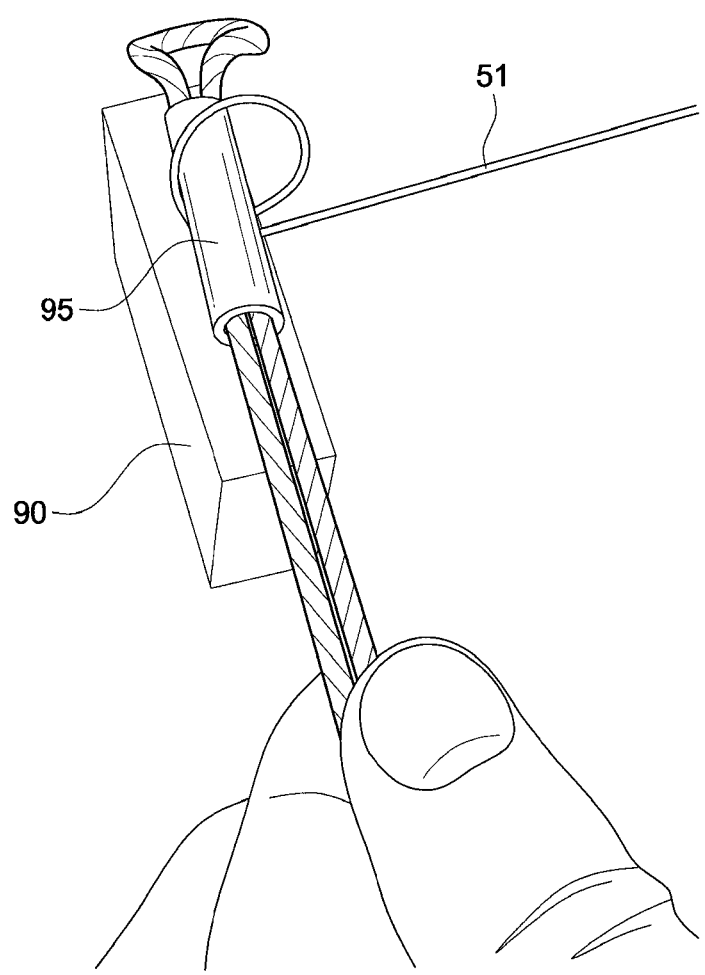
Figure 11:
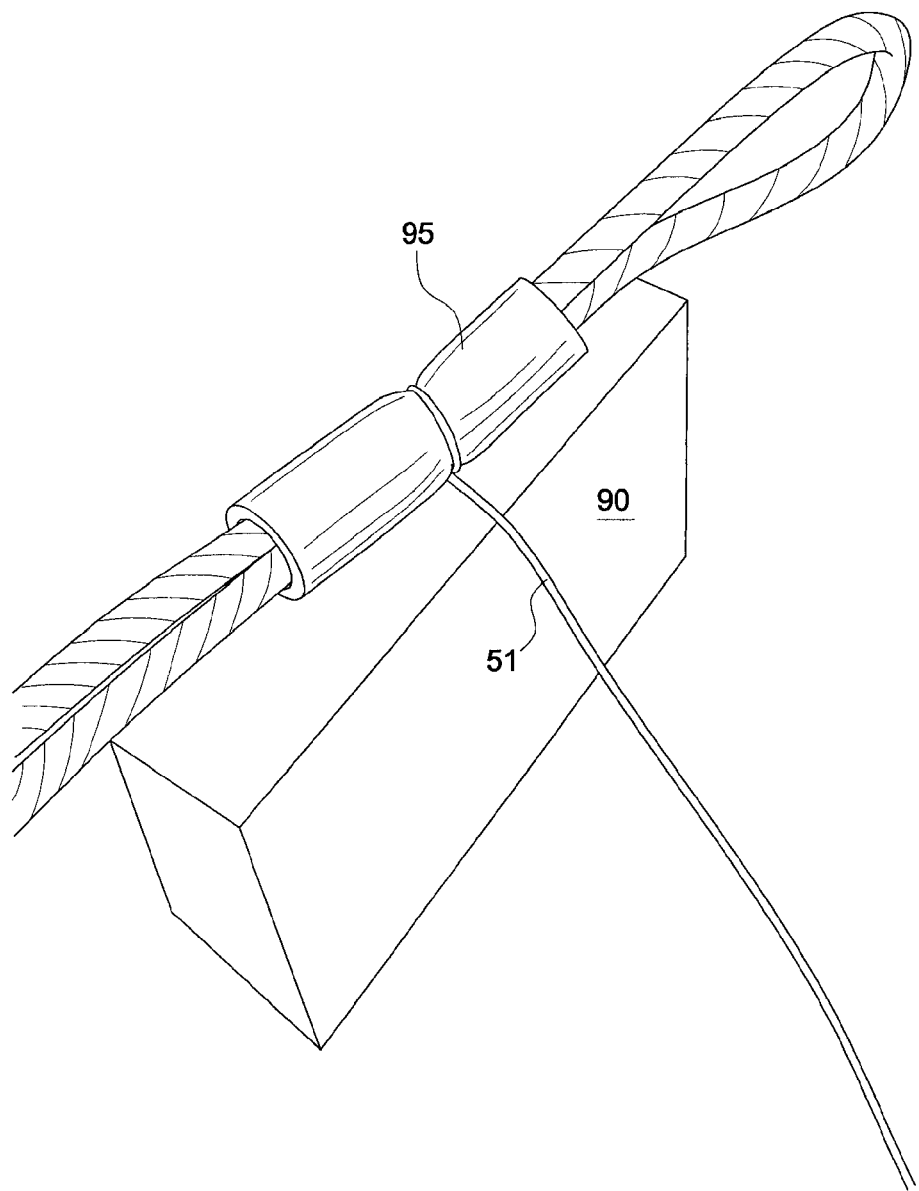

FIGS. 6-11 illustrate details of forming the self-cinching construct 50 with cinching loop 55 of soft, knotless anchor 200 and methods of attaching tissue to bone by employing such construct. FIGS. 6-8 illustrate in more detail the splicing of the cinching suture 51, at the splice region 53. FIG. 9 illustrates the insertion of soft, knotless anchor 200 into drilled hole 99 formed within bone 90. FIGS. 10 and 11 illustrate the self-cinching construct 50 with cinching loop 55 of soft, knotless anchor 200 passed around tissue 95 which is to be secured to bone 90. By pulling on the free end of the cinching suture 51, the perimeter of the adjustable, cinching loop 55 decreases around the tissue 95 and approximates the tissue 95 to bone 90, at the desired location and under the desired tension.

Figure 12:
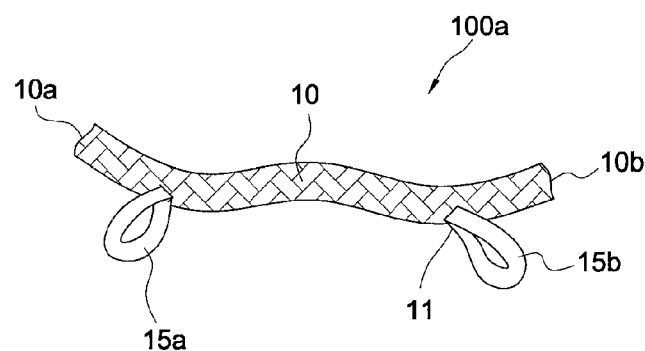
FIG. 12 illustrates a soft anchor according to another exemplary embodiment of the present invention.
Figure 13:
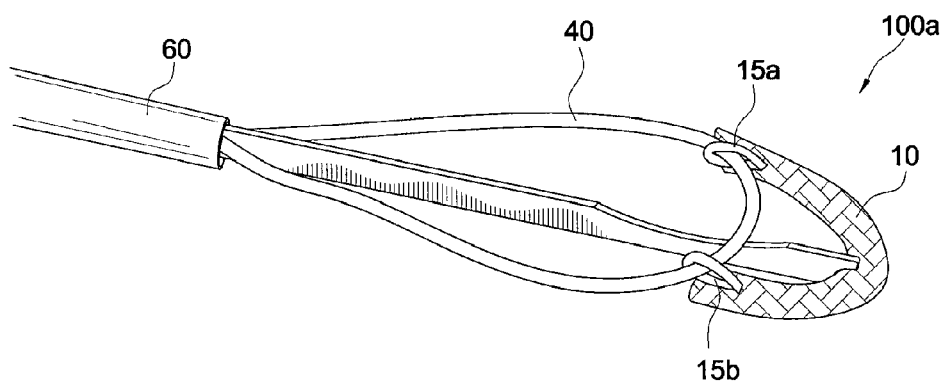
FIG. 13 illustrates the soft anchor of FIG. 12 with at least one sliding suture passing through the eyelets of the anchor and secured to an inserter instrument.

FIGS. 12 and 13 illustrate yet another exemplary embodiment of a soft anchor 100a of the present invention. Soft anchor 100a is similar to the soft anchor 100 of FIGS. 1-4 in that it is also a knotted anchor (i.e., allows attachment of a tissue attachment strand that will secure tissue by tying knots) but differs in that the securing strand 11 forms two small eyelets/loops 15a, 15b that allow tissue attachment strand 40 to attach thereto and pass slidingly there through. Anchor body 10 of soft anchor 100a is similar to anchor body 10 of anchor 100 in that it is also formed essentially of a soft material (for example, coreless suture such as a polyester braided sheath/sleeve) that may have a sleeve/sheath/tubular configuration with open or closed ends and/or may be a hollow construct. Anchor body 10 of soft anchor 100a may be any woven, knitted, or braided structure formed of various yarns, fibers and/or filaments, and typically without a core.

Securing strand 11 could be any type of suture (including coreless suture) that has a dumbbell configuration with two small eyelets 15a, 15b (as shown in FIG. 12). Strand 11 can extend through the cannulation of the sleeve/sheath 10 and through the open ends 10a, 10b, or through an opening in the sleeve body 10. The securing strand 11 accommodates the tissue attachment strand 40.

Figure 21:
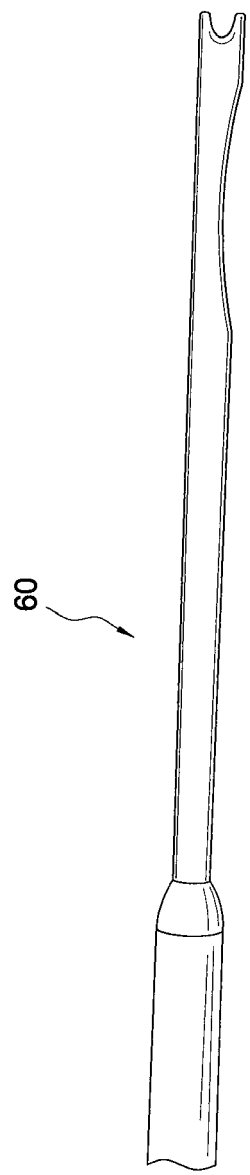
FIG. 21 illustrates an exemplary embodiment of an inserter of the present invention.

FIG. 13 illustrates tissue attachment strand 40 passed through eyelets 15a, 15b of securing strand 11 and further secured to inserter 60 (pre-assembled with the anchor to inserter 60). Strand 40 attaches to the tissue to be fixated and forms knots for securing the tissue repair for the knotted embodiments. A more detailed depiction of inserter 60 is shown in FIG. 21.

Figure 14:
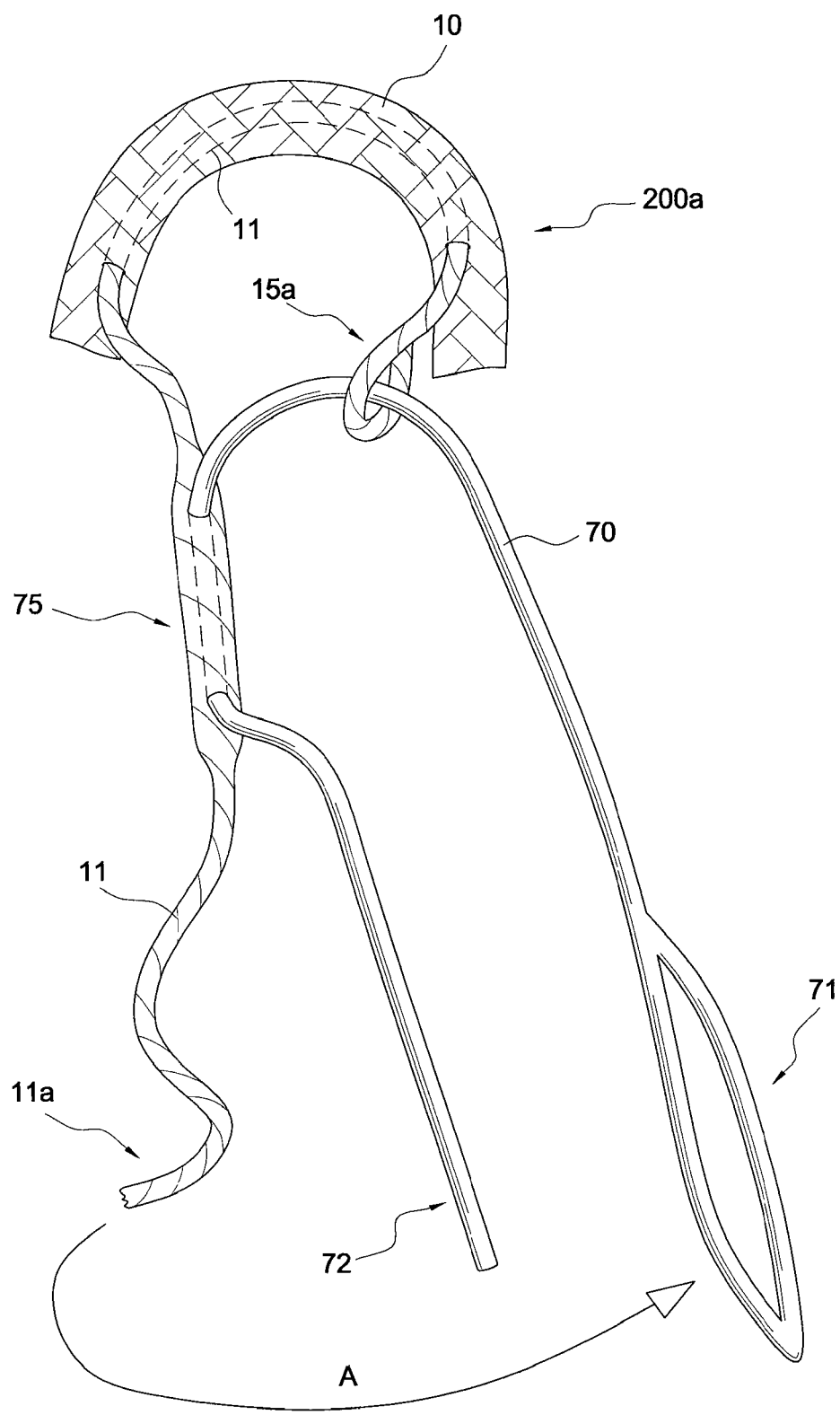
FIGS. 14 and 15 illustrate steps of forming a soft anchor according to yet another exemplary embodiment of the present invention (a knotless soft suture with a self-cinching loop).
Figure 15:
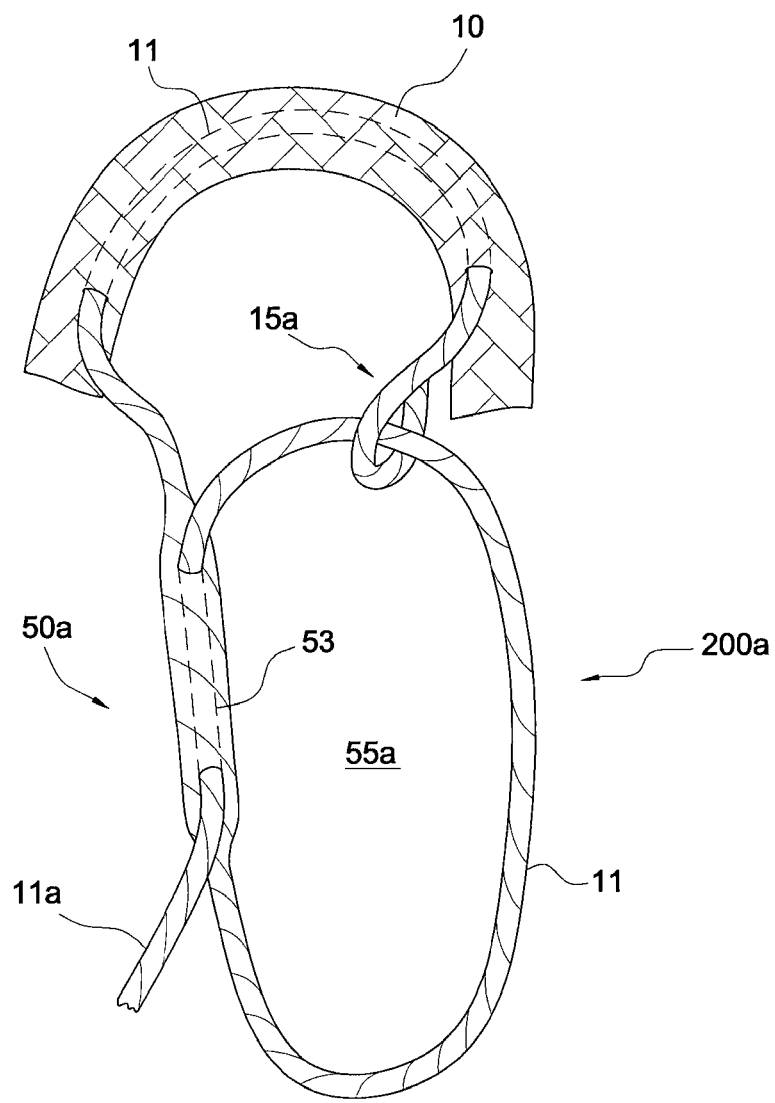

FIGS. 14 and 15 illustrate yet another embodiment of soft anchor 200a of the present invention. Anchor 200a is similar to soft anchor 200 of FIG. 5 in that it is also a knotless soft anchor which has an anchor body 10 similar to anchor body 10 of soft anchor 200. However, anchor 200a differs from anchor 200 in that the securing strand 11 is provided with only one eyelet 15a (located at one end of the strand) and preloaded with a shuttle/pull device 70 (a suture passer 70 such as a nitinol passing wire 70) attached at the portion of the strand that exits the anchor body (for example, at a portion of the other end of the strand). Suture passer 70 is pre-assembled to the securing strand 11 as shown in FIG. 14 and will form a splice loop 55a shown in FIG. 15 during the repair. Securing strand 11 could be any flexible strand such as suture or suture tape, preferably without a core to make the splice easier. The securing strand 11 becomes the tissue attachment suture, but without requiring a knot to secure the tissue since the splice accomplishes the locking. An attaching suture is also attached to the anchor to provide for pre-assembly of the construct to the inserter 60. The attaching suture is removed once the anchor is placed in the bone hole/socket.

The free end 11a of strand 11 is passed through eyelet 71 of the suture passer 70 (in the direction of arrow A of FIG. 14) and then the suture passer 70 is pulled to allow strand 11 to pass through itself at the region 53 (FIG. 15) and form splice 53 and self-cinching adjustable flexible loop 55a (FIG. 15). The perimeter of flexible loop 55a is adjustable, to allow the construct to be self-cinching and to adjust the tension on the tissue to be fixated.

An exemplary knotless method of fixation of soft tissue to bone with soft anchor 200a of the present invention comprises inter alia the steps of: (i) after insertion of anchor 200a and removal of inserter 60, suture 11 is passed around or through tissue 95 desired to be fixed; (ii) next, free end 11a of strand 11 is fed through wire eyelet 71; (iii) wire end 72 is pulled which causes the construct to be created by causing the free end 11a of strand 11 to pass through eyelet 15a, followed by the free end 11a of strand 11 to pass through splice area 53 and form adjustable knotless closed loop 55a; and (iv) wire 70 is discarded and the free end 11a of strand 11 is tensioned to desired repair approximation.

FIGS. 16-20 illustrate subsequent steps of a method of tissue fixation (tissue approximation/repair) with exemplary soft anchor 200a of the present invention. Inserter 60 (FIG. 16) pushes soft anchor 200a within bone hole 99 formed in bone 90. FIG. 17 shows the sheath 10 (anchor body 10) bunched up within the bone hole 99, i.e., from a non-compressed, initial length $L_1$ (FIG. 16) to a compressed, bunched up, final length $L_2$ (FIG. 17).

Soft anchor 200a is provided pre-assembled with shuttle/pull device 70 (nitinol passing wire 70) attached to strand 11 (at splice area 75) and passing through eyelet 15a. Free end 11a of strand 11 is passed through the nitinol wire eye 71 (in the direction of arrow A) and around exemplary soft tissue 95 to be attached to bone 90, as shown in FIG. 17. Tensioning on the wire end 72 pulls the suture end 11a through the construct (FIG. 18).

Figure 20:
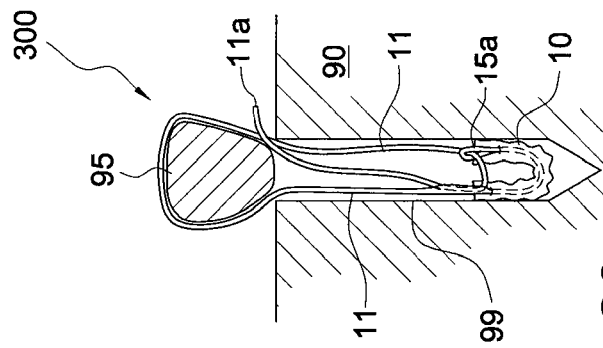
Figure 19:
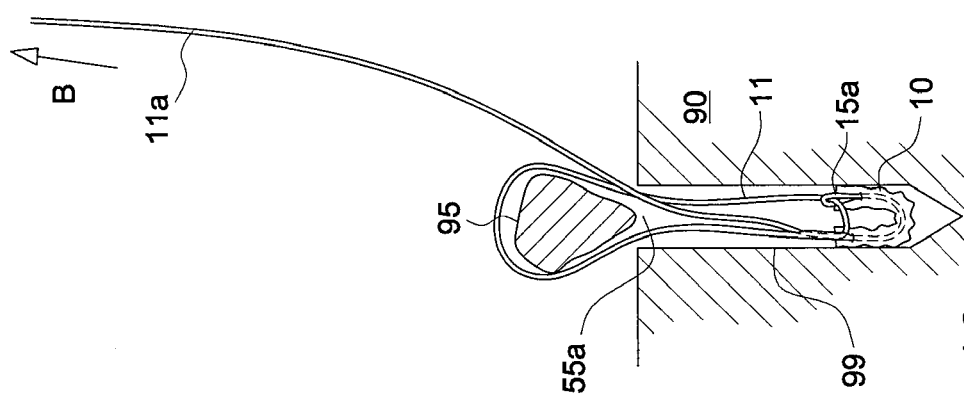

Wire passer 70 is removed and tension is applied on the suture end 11a of strand 11, as shown in FIG. 19 (by pulling in the direction of arrow B) to form adjustable closed loop 55a that is tightened on and around tissue 95. FIG. 20 illustrates final repair 300 with sheath 10 (anchor body 10) bunched up within the bone hole 99 and securing strand 11 around soft tissue 95 approximated to bone 90 by adjustable, knotless self-cinching flexible spliced loop 55a.

The materials employed for the formation of the soft anchors 100, 200, 100a, 200a may be loosely braided polyester sutures, which may be braided with at least one other fiber, natural or synthetic, to form lengths of suture material. The suture-based anchors 100, 200, 100a, 200a may be also formed of suture tape. The suture tapes may have the same, uniform width or may have different widths, and may comprise the same or different materials.

The flexible, soft material forming the soft anchors 100, 200, 100a, 200a may be also formed of suture tape or a combination of suture and tape, a stiff material, or combination of stiff and flexible materials, depending on the intended application. Alternatively, the flexible material may be formed in the shape of a folding tube suture anchor which may contain textile or homogenous material. The folding tube anchor may be formed of a tube (cylinder or sleeve/sheath) provided with apertures/holes to allow the flexible strands to pass therethrough. When the tube is inserted into a bone tunnel/socket and when tension is applied, the tube folds and lodges into the bone tunnel/socket but the tying, sliding sutures remain free for additional manipulation and surgical procedures.

As noted above, the soft anchors 100, 200, 100a, 200a may be formed of any soft materials such as yarns, fibers, filaments, strings, fibrils, strands, sutures, etc. or combinations of such soft materials. The soft materials may be woven, braided, knitted or otherwise interlocked with each other to achieve the soft anchors of the present invention. The soft materials may be synthetic or natural materials, or combinations of synthetic and natural materials. The anchors 100, 200, 100a, 200a may be in the form of any sleeve/sheath/tubular structure which may be provided with open or closed ends, or with at least one open end or with at least one closed end. The anchors 100, 200, 100a, 200a may also have a tubular or cylindrical shape, partially tubular shape, a sleeve-like shape, or may be in the form of any hollow or partially hollow shape construct provided with a cannulation extending at least along a portion of the length of the structure. The anchors 100, 200, 100a, 200a may be woven or braided structures, or may be formed of yarns, fibers or similar materials, or combinations of these materials, that are joined/interlocked together by any known method in the art. In the exemplary-only embodiments above, the soft anchors 100, 200, 100a, 200a of the present invention are suture-based anchors formed essentially of suture such as braided polyester or polyethylene.

As noted above, the soft anchors 100, 200, 100a, 200a detailed above may be also employed with a self-cinching suture mechanism that could be incorporated into the implant/anchor. Once the anchor is deployed, the surgeon would simply pull on the self-cinching suture strands to firmly secure the device and compress the tissue (for example, the rotator cuff). The soft anchors 100, 200, 100a, 200a could be utilized for multiple additional indications such as, for example, AC joint reconstruction, syndesmosis reconstruction, quad/patellar tendon rupture repair, hallux-valgus repair, and any other tendon repair to bone.

The soft anchors 100, 200, 100a, 200a detailed above may be also employed in conjunction with additional various knotted and/or knotless fixation devices (or combination of such knotted and knotless fixation devices), such as hard suture anchors to secure, for example, a medial row on rotator cuff repairs.

The flexible strands 11, 40 employed for the formation of the soft anchors 100, 100a, 200, 200a may be high-strength sutures, such as the high strength suture sold by Arthrex, Inc. of Naples, Fla. under the registered tradename TigerWire® or FiberWire®, which is disclosed and claimed in U.S. Pat. No. 6,716,234, the entire disclosure of which is incorporated by reference in its entirety herewith. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strands may be also formed of suture tape or a suture chain. The suture tapes may have the same, uniform width or may have different widths, and may comprise the same or different materials.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:

1. A soft anchor for surgical repairs comprising:
an anchor body formed of a flexible material designed to be compressed from a first, non-compressed position to a second, compressed position, the anchor body including first and second openings; and
at least one flexible strand attached to the anchor body, the flexible strand extending through the anchor body such that a first end of the flexible strand extends through the first opening and a second end of the flexible strand extends through the second opening, the first end of the flexible strand terminating in an eyelet, and the second end extending through the eyelet and extending through a splice in the second end of the flexible strand to form a closed loop.

2. The soft anchor of claim 1, wherein the closed loop forms a self-cinching flexible closed loop with an adjustable perimeter.

3. The soft anchor of claim 1, wherein the at least one flexible strand, when pulled, is designed to compress the flexible material from the first, non-compressed position to the second, compressed position.

4. The soft anchor of claim 1, wherein the anchor body is in the form of a sleeve, a sheath, a tube or a hollow construct.

5. The soft anchor of claim 1, wherein the anchor body is a braided sheath formed of polyester.

6. The soft anchor of claim 1, wherein the at least one flexible strand is a suture strand or a suture tape.

7. The soft anchor of claim 1, wherein the anchor is knotted or knotless.

8. A soft anchor for fixation of soft tissue to bone, comprising:
a tubular sleeve formed of a flexible material, a cannulation and two ends;
a flexible strand with a first end and a second end, the flexible strand extending through at least a portion of the cannulation of the tubular sleeve and with the first end exiting a first opening of the tubular sleeve and with the second end exiting a second opening of the tubular sleeve, the first end terminating in an eyelet; and a shuttling device having one portion coupled to the second end of the flexible strand and another portion extending through the eyelet of the first end of the flexible strand, wherein the second end of the flexible strand passes through the eyelet at the first end and passes through a splice in the second end of the flexible strand, to form a closed loop having an adjustable perimeter.

9. The soft anchor of claim 8, wherein the tubular sleeve is formed of a coreless braid of polyester or polyethylene.

10. The soft anchor of claim 8, wherein the flexible strand is a coreless suture.

11. The soft anchor of claim 8, wherein the anchor is a suture-based anchor.

12. The soft anchor of claim 8, wherein the shuttling device is a nitinol suture passer.

13. A method of knotless fixation of soft tissue to bone, comprising the steps of:

providing a soft anchor comprising a tubular sleeve or sheath formed of a flexible material and having a first length, a cannulation and two ends; and a flexible strand attached to the tubular sleeve, the flexible strand forming an eyelet at a first end and having a shuttling device attached to a portion of a second end of the flexible strand;

inserting the soft anchor into a socket or tunnel formed into bone so that the soft anchor bunches up within the socket or tunnel;

passing the second end of the flexible strand around tissue to be fixated and then through an eyelet of the shuttling device;

pulling the shuttling device so that the second end of the flexible strand passes through the eyelet of the first end of the flexible strand and then passes through the second end of the flexible strand to form a splice through itself and a self-cinching closed loop with an adjustable perimeter;

removing the shuttling device; and pulling on the second end to provide tensioning of soft tissue relative to the bone.

14. The method of claim 13, wherein the shuttling device is a suture passer.

15. The method of claim 13, further comprising the step of securing the soft anchor to an inserter or driver.

16. The method of claim 13, further comprising the step of providing an attachment suture pre-assembled with the anchor to hold the anchor onto an inserter.

* * * * *